United States Patent [19]

Watanabe et al.

[11] Patent Number: 4,975,514

[45] Date of Patent: Dec. 4, 1990

[54] POLYURETHANE ELASTOMER FORMED FROM AN AMIDE-MODIFIED POLYISOCYANATE

[75] Inventors: Hiroyuki Watanabe; Hiroshi Washita; Kazuhiko Kuga, all of Kanagawa, Japan

[73] Assignee: Asahi Glass Company, Ltd., Tokyo, Japan

[21] Appl. No.: 349,967

[22] Filed: May 8, 1989

Related U.S. Application Data

[62] Division of Ser. No. 174,364, Mar. 28, 1988, abandoned.

[30] Foreign Application Priority Data

Mar. 31, 1987 [JP] Japan ................................. 62-76346

[51] Int. Cl.$^5$ ...................... C08G 18/70; C08G 18/73
[52] U.S. Cl. ......................................... 528/60; 528/64; 528/65; 528/66; 560/351; 560/355; 560/359
[58] Field of Search ...................... 560/351, 355, 359; 528/60, 64, 65, 66

[56] References Cited

U.S. PATENT DOCUMENTS

| | | | |
|---|---|---|---|
| 3,517,039 | 6/1970 | Wagner et al. | 560/359 |
| 3,959,348 | 5/1976 | Reiff et al. | 560/351 |
| 4,105,686 | 8/1978 | Raes et al. | 560/351 |
| 4,187,366 | 2/1980 | Friedlander et al. | 528/75 |
| 4,197,374 | 4/1980 | Narayan et al. | 560/359 |
| 4,322,364 | 3/1982 | Hughes et al. | 560/351 |
| 4,652,494 | 3/1987 | Bravet et al. | 428/423.1 |

FOREIGN PATENT DOCUMENTS 2359613 6/1975 Fed. Rep. of Germany ...... 560/351

*Primary Examiner*—John Kight, III
*Assistant Examiner*—Dennis R. Daley
*Attorney, Agent, or Firm*—Oblon, Spivak, McClelland, Maier & Neustadt

[57] ABSTRACT

A polyisocyanate composition containing an amide-modified product, obtained by modifying a polyisocyanate compound with a polybasic carboxylic acid in an equivalent ratio of carboxyl groups/isocyanate groups being at most 0.9.

10 Claims, No Drawings

POLYURETHANE ELASTOMER FORMED FROM AN AMIDE-MODIFIED POLYISOCYANATE

This application is a division of application Ser. No. 07/174,364, filed on Mar. 28, 1988, now abandoned.

The present invention relates to a novel polyisocyanate composition.

Polymers such as polyurethane, polyurethane urea, polyurea and polyisocyanurate are prepared by using a polyisocyanate compound as one of the main starting materials. For example, foams, sheets, films or other shaped products of polyurethane or coating materials, adhesives, water repellants and sealants are produced by using a polyisocyanate compound and a polyol as the main starting materials. In order to obtain desired characters or properties for a polymer prepared from a polyisocyanate compound as a starting material, it is common in most cases to pay attention primarily to the selection of additives or starting materials other than the polyol and the polyisocyanate compound. However, in some cases, the selection of the polyisocyanate compound is also an important factor. Accordingly, it is known, for example, to use two or more polyisocyanate compounds in combination or to modify a polyisocyanate compound by various compounds or by various treating methods in order to obtain the desired properties. Specific examples of such modified polyisocyanate compounds include prepolymer-type modified products which have been modified by a polyhydric alcohol such as trimethylol propane and urea modified products which have been modified by an amine or water as well as trimers (nurate modified products), carbodiimide-modified products, buret-modified products, etc. It happens not infrequently that a so-called modified product is in fact a mixture of a modified product and a non-modified product. The polyisocyanate compound composition of the present invention, which will be described hereinafter, is a composition comprising a modified polyisocyanate compound i.e. modified by a certain specific compound and a polyisocyanate compound not modified by such a compound. The polyisocyanate compound referred to hereinafter includes a modified polyisocyanate compound other than the one modified by this specific compound.

For the production of a polymer obtainable by using a polyisocyanate compound as the starting material such as polyurethane (hereinafter referred to as an isocyanate polymer), it is common to firstly produce a mixture of a polyisocyanate compound with other starting materials (hereinafter referred to as a reactive mixture) and then produce an isocyanate polymer from this mixture. It is preferred that the polyisocyanate polymer thereby obtained has high strength. However, it has been common to impart such high strength by increasing the content of an expensive isocyanate compound, and there has been a drawback that the price of the product is thereby high. It is also known to impart high strength by using a modified polyisocyanate compound. For example, Japanese Unexamined Patent Publication No. 135216/1984 and U.S. Pat. No. 4,652,494 disclose that an isocyanate modified by urea is prepared by the reaction of a diisocyanate with water, and it is used as a starting material for the isocyanate polymer to obtain the isocyanate polymer having high strength. However, according to this method, the resulting urea-modified product has high crystallizability, and its content is obliged to be limited. Further, even if the content of the urea-modified product is controlled to impart high strength, the resulting composition will be highly viscous and there will be difficulty in its handling.

Accordingly, a polyisocyanate composition useful as a starting material for a highly strong isocyanate polymer having low crystallizability and low viscosity, is desired.

It is an object of the present invention to overcome the above problems and to provide an amide-modified organic polyisocyanate composition containing a reaction product of a polybasic carboxylic acid with an organic polyisocyanate compound in an amount stoicheometrically in excess of said polybasic carboxylic acid.

Namely, the present invention provides a polyisocyanate composition containing an amide-modified product, obtained by modifying a polyisocyanate compound with a polybasic carboxylic acid in an equivalent ratio of carboxyl groups/isocyanate groups being at most 0.9.

Now, the present invention will be described in detail with reference to the preferred embodiments.

The reaction product of the polybasic carboxylic acid with the polyisocyanate compound in the present invention is not necessarily limited to a compound having a single structure. Of course, in some cases, a compound of a single structure may form. However, when the polybasic carboxylic acid has two or more isocyanate reactive groups, the product is considered to be a mixture of various compounds.

Some reaction products of a polybasic carboxylic acid and a polyisocyanate compound are known. In most cases, however, in such reaction products, the equivalent ratio of carboxyl groups (—COOH)/isocyanate groups (—NCO) is substantially 1, and it is intended to obtain polyamides, i.e. no particular attention has been paid to the terminal isocyanate group. It is not the main purpose of the present invention to improve the properties of polyamide resins such as the heat resistance. In the present invention, the equivalent ratio of —COOH/—NCO is required to be at most 0.9. The upper limit is preferably 0.5 in view of the viscosity, and the lower limit is preferably 0.001 with a view to imparting high strength to the product. A particularly preferred equivalent ratio is from 0.01 to 0.2. The composition of the present invention can be obtained usually by adding and reacting the polybasic carboxylic acid to the isocyanate compound, or after the reaction further diluting the reaction product with a polyisocyanate compound. If necessary, the composition may be diluted with a solvent inert to an isocyanate group to obtain a solution. The polybasic carboxylic acid in the present invention may be an aliphatic, alicyclic or aromatic polybasic carboxylic acid having 2 or more carboxyl groups such as a dicarboxylic acid, a tricarboxylic acid or a tetracarboxylic acid. For example, there may be mentioned an aliphatic dicarboxylic acid of the formula $HO_2C(CH_2)_nCO_2H$ wherein n is an integer of 0 or more, such as oxalic acid, malonic acid, valeric acid or adipic acid, an aromatic dicarboxylic acid such as phthalic acid, o-phthalic acid or terephthalic acid, an aromatic tricarboxylic acid such as trimellitic acid, an aromatic tetracarboxylic acid such as pyromellitic acid. Further, it may be a polymer or copolymer of a vinyl monomer having a carboxyl group such as a polymer of acrylic acid or methacrylic acid, or a copolymer of acrylic acid or methacrylic acid with other vinyl monomers.

As the polyisocyanate compound in the present invention, compounds having at least two isocyanate groups in their molecules may be used alone or in combination of two or more. The polyisocyanate compounds include aliphatic, alicyclic and aromatic polyisocyanates and their modified products (excluding modified products according to the present invention). For example, there may be mentioned hexamethylene diisocyanate, octamethylene diisocyanate, trimethylhexamethylene diisocyanate, lysine diisocyanate, isophorone diisocyanate, hexahydrotolylene diisocyanate, bis(isocyanatemethyl)cyclohexane, methylenebis(cyclohexylisocyanate), cyclohexane diisocyanate, xylylene diisocyanate, tolylene diisocyanate, diphenylmethane diisocyanate, phenylene diisocyanate, polymethylenepolyphenyl isocyanate, tolidine diisocyanate, triphenylmethane triisocyanate or tris(4-isocyanatephenyl)thiophosphate. Further, a homopolymer or copolymer of an isocyanate group-containing vinyl monomer, for example, a homopolymer of a (meth)acrylate having an isocyanate alkyl group (particularly α-isocyanate ethyl methacrylate), or methaisopropenyl-α,α-dimethylbenzyl isocyanate, or its copolymer with a copolymerizable monomer such as an alkyl (meth)acrylate or styrene, is also useful as the polyisocyanate compound in the present invention. The modified products include prepolymer type modified products modified with polyhydric alcohols or other polyols, urea-modified products modified with polyamines or water, carbodiimide-modified products, buret-modified products, trimers, dimers and other modified products.

The polyisocyanate composition of the present invention is obtained usually by dispersing the polybasic carboxylic acid in the excess equivalent amount of the polyisocyanate compound and reacting them. The composition thus obtained may be diluted by an addition of a polyisocyanate compound, if necessary. The production of the composition may be conducted in the presence of an inert solvent. Otherwise, after completion of the reaction, the composition may be diluted with a solvent.

The polyisocyanate composition of the present or a mixture of the amide-modified product and unreacted polyisocyanate compound. Further, it may be mixture obtained by further adding a polyisocyanate compound to the above amide-modified product or to the mixture containing it (i.e. by diluting with a polyisocyanate compound). The additional polyisocyante compound may be the same or different polyisocyanate compound as used in the reaction. The ratio of the amide-modified product in the polyisocyanate composition is, as expressed by the equivalent ratio of —COOH/—NCO in the polybasic carboxylic acid and the polyisocyanate compound used (including a polyisocyanate compound used for dilution), is at most 0.9, preferably within a range of from 0.001 to 0.5, particularly preferably from 0.01 to 0.2. Further, there is no particular restriction as to the content of isocyante groups in the composition of the present invention. However, it is preferably at least 10%, particularly preferably from 20 to 50%.

In addition to the reaction product and unreacted polyisocyanate compound, other additives may be incorporated to the composition of the present invention. Such additives may be incorporated preliminarily to the polyisocyanate compound or the polybasic carboxylic acid before the reaction, so long as they do not adversely affect the reaction. Such additives include stabilizers such as an antioxidant, a ultraviolet absorber or a light stabilizer, coloring agents, fillers and foaming agents. Further, depending upon the particular purpose, a blocking agent may be reacted to the composition of the present invention to obtain a composition containing a blocked isocyanate compound or a blocked reaction product.

The polyisocyanate composition of the present invention may be used for the same applications as usual polyisocyanate compounds. Particularly, it is suitable as a starting material for an isocyanate polymer. Namely, it may be reacted with at least one compound having at least two isocyanate reactive groups to obtain an addition polymerization or condensation polymerization-type polymer. For example, when reacted with a polyol, it produces a polyurethane, and when reacted with a polyol and a polyamine, it produces a polyurethane urea. If reacted with a polyurethane in the presence of a trimerizing catalyst, it produces a polyurethane-modified polyisocyanurate. When reacted with a polyamine or water, it produces a polyurea. When reacted with a polycarboxylic acid or a polycarboxylic anhydride, it produces a polyamide or a polyamideimide. The composition of the present invention is particularly suitable as a starting material for a polyurethane polymer such as polyurethane or polyurethane urea.

The polyurethane polymer is a polymer obtained by reacting a polyol or a polyol and a polyamine to a polyisocyanate compound. The polyol includes a high molecular weight polyol such as polyether polyol, polyester polyol, polycarbonate polyol or an addition polymerization type polymer having at least two hydroxyl groups (such as a butadiene type polymer or a hydroxyalkyl (meth)acrylate type polymer) and a low molecular weight polyol such as a polyhydric alcohol which is called a chain extender or a cross-linking agent. The polyamine includes a relatively low molecular weight polyamine which is called a chain extender or a cross-linking agent and a relatively high molecular weight polyamine such as a polyoxyalkylene having at least two amine groups at the molecular terminals. The composition of the present invention is particularly suitable for use for the production of a polyurethane polymer which is obtainable by using a relatively high molecular weight polyol and a chain extender or a cross-linking agent.

As mentioned above, the composition of the present invention is effective when used in a field of producing an isocyanate polymer required to have high strength, particularly a polyurethane polymer. Specifically, it is useful for the production of a film, sheet or other shaped product, the production of a foam by molding by means of a mold, the production of a shaped product by reaction injection molding and the application to the field of coating materials or adhesives. Among the above applications, it is particularly suitable as a starting material for a polyurethane polymer elastomer. As will be described hereinafter, a polyurethane polymer elastomer obtained by using the composition of the present invention as a starting material, has substantially improved tensile strength or tear strength without any substantial deterioration of its breaking extension. These properties indicate that the composition of the present invention is particularly suitable as a starting material for films or sheets. Such a film or sheet can be produced by using a relatively high molecular weight polyol, a chain extender (or cross-linking agent) and the composition of the present invention in an amount of from 0.8 to 1.3 times by equivalent relative to the total equivalent amount of the polyol and chain extender (or cross-linking agent), as the main starting materials. The relatively high molecular weight polyol is preferably a polyol having a hydroxyl value of from about 20 to about 120 and from 2 to 3 hydroxyl groups, such as a polyester type polyol, a polycarbonate type polyol or a polyoxytetramethylene polyol. The chain extender (or cross-linking agent) is preferably a polyol or polyamine having a molecular weight of at most 400. For exmaple, it may be ethylene glycol, 1,4-butane diol, cyclohexane dimethanol, dimethylolpropionic acid, hexamethylene diamine, isophorone diamine or dicyclobenzidine.

The composition of the present invention is most suitable as the starting material for films or sheets useful for a laminated safety glass. The film or sheet useful for a laminated safety glass may be used for a laminated glass type or bilayer type laminated safety glass. Polyurethane polymer elastomers of this type are disclosed in e.g. U.S. Pat. No. 4,103,070, Japanese Examined Patent Publication No. 9582/1983, U.S. Pat. Nos. 3,900,446, 4,643,944, European Pat. Nos. 133,090, 131,523, U.S. Pat. No. 4,652,494 and Japanese Unexamined Patent Publication No. 281118/1986. The composition of the present invention can be used as the polyisocyanate compound for the preparation of such elastomers. For this purpose, the composition of the present invention is preferably a non-yellowing type. Namely, among those mentioned above, non-yellowing ployisocyanates such as an aliphatic polyisocyanate, alicyclic polyisocyante and an aromatic polyisocyanate wherein isocyanate groups are not directly attached to the aromatic ring, such as xylylene diisocyanate. Particularly preferred is an aliphatic polyisocyanate such as 1,6-hexanediisocyanate, or an alicyclic polyisocyanate such as isophorone diisocyanate or methylene bis(cyclohexylisocyanate).

Now, the present invensiton will be described in further detail with reference to Examples. However, it should be understood that the present invention is by no means restricted to such specific Examples.

EXAMPLE 1

Into a 3 liter separable flask equipped with a mechanical stirrer, a Liebig condenser and a nitrogen supply tube, 1,904.2 g of isophorone diisocyanate and 95.8 g of adipic acid were introduced. The mixture was stirred while introducing dry nitrogen gas. After the adipic acid was uniformly dispersed, the temperature was raised to 130° C. over a period of 2 hours. Then, the reaction was continued for 4 hours. The reaction mixture was left to cool. The polyisocyanate composition thereby obtained was a slightly yellow liquid with a NCO content of 32.58%.

EXAMPLE 2

A polyisocyanate composition was prepared in the same manner as in Example 1 by using 1,927.9 g of hexamethylene diisocyanate and 72.06 g of succinic acid. The polyisocyanate composition thereby obtained was a slightly yellow liquid with a NCO content of 44.2%.

EXAMPLE 3

A polyisocyanate compositon was prepared in the same manner as in Example 1 by using 1,858.2 g of TDI-80 (mixture of 2,4-tolylene diisocyanate/2,6-tolylene diisocyanate in a weight ratio of 80/20) and 141.8 g of isophthalic acid. The polyisocyanate composition thereby obtained was a slightly yellow liquid with a NCO content of 37.5%.

EXAMPLE 4

3,000 g of polybutylene adipate diol having a hydroxyl value of 55.1 was heated and stirred under vacuum of 3 mmHg at 110° C. for 2 hours for degassing and dehydration. Then, 1,588.77 g of the polyisocyanate composition obtained in Example 1, and 0.3 g of dibutyltin dilaurate were added thereto, and the mixture was reacted at 80° C. for 20 minutes under a nitrogen atmosphere. Then, 411.29 g of 1,4-butane diol was added to the reaction mixture and promptly mixed by stirring. Heat was generated by the initiation of the raction. After the reaction mixture was thoroughly mixed to be substantially uniform, this reaction resin solution was poured into a dried vessel coated with polytetrafluoroethylene and reacted at 130° C. for about 15 hours under a nitrogen atmosphere. The polymer thereby obtained was cooled to room temperature, pulverized by a pulverizer and pelletized by pelletizer. The pellets thereby obtain was formed into a transparent polyurethane sheet having a thickness of 0.5 mm by a conventional method by means of an extruder at a fusing temperature of from 180° to 220° C. The physical properties of the sheet are shown in Table 1.

EXAMPLE 5

In the same manner as in Example 4, a transparent polyurethane sheet having a thickness of 5 mm was prepared by using 3,000 g of polybutylene adipate having a hydroxyl value of 55.1, 1,456.17 g of the polyisocyanate composition obtained in Example 2, 0.30 g of dibutyltin dilaurate and 543.89 g of 1,4-butane diol. The physical properties of the sheet are shown in Table 1.

EXAMPLE 6

In the same manner as in Example 4, a transparent polyurethane sheet having a thickness of 0.5 mm was prepared by using 3,000 g of polybutylene adipate having a hydroxyl value of 55.1, 1,529.67 g of the polyisocyanate composition obtained in Example 3 and 470.39 g of 1,4-butane diol. The physical properties of the sheet are shown in Table 1.

EXAMPLE 7

16.28 g of polycaprolactone diol having a hydroxyl value of 92.3, 73.27 g of poly(alkylenecarbonate) diol having a hydroxyl value of 66.3 (which is a carbonate diol prepared from 1,6-hexane diol and 1,4-cyclohexane dimethanol) and 73.27 g of polycaprolatone triol having a hydroxyl value of 112.3, were heated and stirred under vacuum of 3 mmHg at 110° C. for 2 hours, for degassing and dehydration. After cooling the mixture to 80° C., 13.51 g of 1,4-butane diol was added and uniformly mixed thereto. Then, 73.66 g of the polyisocyanate composition obtained in Example 1, and 0.015 g of dibutyltin dilaurate were added thereto and promptly mixed by stirring. Heat was generated by the initiation of the reaction. After the reaction mixture was thoroughly mixed to be substantially uniform, it was thoroughly degassed, cast in a thickness of 1 mm on a glass plate treated for releasing and reacted at 140° C. for 40 minutes under a nitrogen atmosphere, to obtain a transparent specular glass-like sheet.

This sheet was cut into a size of 30×30 cm and sandwiched between a pair of glass plates having a size of 30×30 cm, and the assembly was introduced into an autoclave. One of the glass plates were preliminarily treated for releasing by applying a polydimethylsiloxane uniformly on the surface to be brought in contact with the sheet. On the surface of the other glass plate to be contacted with the sheet, α-glycidoxypropyl trimethoxysilane was uniformly coated. The autoclave was initially vacuumed to remove air between the glass plates and the sheet and then heated to 120° C. under vacuum for preliminary press-bonding. Then, the autoclave was maintained at 140° C. under a pressure of 13 kg/cm² for about 30 minutes to completely bond the sheet to the glass plate. Then, the assembly was withdrawn from the autoclave, and the release-treated glass plate was removed to obtain a bilayer glass composed of urethane sheet/glass.

EXAMPLE 8

In the same manner as in Example 7, a transparent specular glass-like sheet having a thickness of 1 mm was prepared by using 76.97 g of polycaprolactone diol having a hydroxyl value of 92.3, 62.98 g of polycaprolactone triol having a hydroxyl value of 112.3, 19.59 g of 1,4-butane diol, 90.45 g of the polyisocyanate composition obtained in Example 1 and 0.015 g of dibutyltin dilaurate, and by using the sheet, a bilayer glass was prepared.

EXAMPLE 9

In the same manner as in Example 7, a transparent specular glass-like sheet having a thickness of 1 mm was prepared by using 101.06 g of polycaprolactone diol having a hydroxyl value of 73.2, 43.31 g of polycaprolactone triol having a hydroxyl value of 200.5, 17.33 g of 1.4-butane diol, 88.30 g of the polyisocyante composition obtained in Example 1 and 0.015 g of dibutyltin dilaurate, and by using the sheet, a bilayer glass was prepared.

COMPARATIVE EXAMPLES 1, 2 and 3

In the same manner as in Example 4, 5 or 6, a polyurethane sheet having a thickness of 0.5 mm was prepared by using isophorone diisocyanate, hexamethylene diisocyanate or TDI-80 instead of the polyisocyanate composition obtained in Example 1, 2 or 3. The physical properties of the sheet are shown in Table 1.

TABLE 1

|  | Example Nos. | | | Comparative Example Nos. | | |
| --- | --- | --- | --- | --- | --- | --- |
|  | 4 | 5 | 6 | 1 | 2 | 3 |
| Isocyanate component | Polyisocyanate composition obtained in Example 1 | Polyisocyanate composition obtained in Example 2 | Polyisocyanate composition obtained in Example 3 | Isophrone diisocyanate | Hexamethylene diisocyanate | TDI-80 |
| Breaking extension (%) | 420 | 580 | 480 | 480 | 630 | 670 |
| Tensile strength (kg/cm²) | 620 | 460 | 420 | 510 | 380 | 320 |
| Tear strength (kg/cm) | 98 | 90 | 81 | 79 | 81 | 57 |

We claim:

1. A polyurethane polymer elastomer obtained by reacting a polyisocyanate composition consisting essentially of an amide-modified product, obtained by modifying a polyisocyanate compound with a polybasic carboxylic acid in an equivalent ratio of carboxyl groups-/isocyanate groups being at most 0.9, a relatively high molecular weight polyol and a chain extender or cross-linking agent selected from the group consisting of ethylene glycol, 1,4-butanediol, cyclohexanedimethanol, dimethylolpropionic acid, hexamethylenediamine, isophorone diamine and dicyclobenzidine.

2. The polyurethane polymer elastomer according to claim 1, wherein the equivalent ratio of carboxyl groups/isocyanate groups is within the range of from 0.001:1 to 0.5:1.

3. The polyurethane polymer elastomer according to claim 2, wherein the equivalent ratio of carboxyl groups/isocyanate groups is within the range of from 0.1:1 to 0.2:1.

4. The polyurethane polymer elastomer according to claim 1, wherein the polyisocyanate compound is a non-yellowing polyisocyante.

5. The polyurethane polymer elastomer according to claim 1, wherein the polybasic carboxylic acid is at least one dicarboxylic acid selected from the group consisting of aliphatic dicarboxylic acids and aromatic dicarboxylic acids.

6. The polyurethane polymer elastomer according to claim 1, wherein the content of the isocyanate groups in the composition is at least 10% by weight.

7. The polyurethane polymer elastomer according to claim 1, which is a transparent polyurethane polymer elastomer.

8. A sheet formed of the transparent polyurethane polymer elastomer as defined by claim 7.

9. The polyurethane polymer elastomer according to claim 1, wherein the chain extender or cross-linking agent is a polyol or a polyamine.

10. The polyurethane polymer elastomer according to claim 1, wherein the chain extender or cross-linking agent is 1,4-butanediol.

* * * * *